US012721952B2

(12) United States Patent
Ducarouge et al.

(10) Patent No.: US 12,721,952 B2
(45) Date of Patent: Sep. 1, 2026

(54) SAFETY SYRINGE

(71) Applicant: Becton, Dickinson and Company, Franklin Lakes, NJ (US)

(72) Inventors: Pierre Ducarouge, Milan (IT); Freddy Mills, Fontanil Cornillon (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 556 days.

(21) Appl. No.: 18/029,130

(22) PCT Filed: Oct. 1, 2021

(86) PCT No.: PCT/US2021/053221
§ 371 (c)(1),
(2) Date: Mar. 29, 2023

(87) PCT Pub. No.: WO2022/072865
PCT Pub. Date: Apr. 7, 2022

(65) Prior Publication Data

US 2023/0364352 A1 Nov. 16, 2023

(30) Foreign Application Priority Data

Oct. 2, 2020 (EP) .................................... 20306146

(51) Int. Cl.
*A61M 5/32* (2006.01)
*A61M 5/31* (2006.01)

(52) U.S. Cl.
CPC ........ *A61M 5/3213* (2013.01); *A61M 5/3137* (2013.01); *A61M 5/326* (2013.01)

(58) Field of Classification Search
CPC ........ A61M 5/3272; A61M 2005/3267; A61M 2005/3258; A61M 5/3271
See application file for complete search history.

(56) References Cited

U.S. PATENT DOCUMENTS 5,429,612 A * 7/1995 Berthier ............. A61M 5/3257 604/110
9,333,306 B2 5/2016 Cross et al.
(Continued)

FOREIGN PATENT DOCUMENTS

CN 103025374 A 4/2013
CN 103068424 A 4/2013
(Continued)

*Primary Examiner* — William R Carpenter
(74) *Attorney, Agent, or Firm* — The Webb Law Firm

(57) ABSTRACT

Provided herein is a safety syringe including a syringe having a barrel having a proximal end, a distal end, and a sidewall therebetween defining an interior, a needle arranged at the distal end of the barrel, and a plunger arranged at the proximal end of the barrel, and a safety subassembly, having a support body having a proximal end, a distal end, and a sidewall therebetween defining an interior, the syringe received within the support body interior, a plurality of finger grips arranged at the proximal end of the support body, and a needle cover arranged at the distal end of the support body and biased distally relative thereto, the needle cover having a proximal end, a distal end configured to contact an injection site of a user, and a sidewall therebetween, the needle cover configured to slide telescopically relative to the support body.

6 Claims, 7 Drawing Sheets

(56) References Cited

U.S. PATENT DOCUMENTS

| | | | | |
|---|---|---|---|---|
| 2003/0212380 | A1 | 11/2003 | Barrelle | |
| 2005/0096598 | A1* | 5/2005 | Crawford | A61M 5/326 604/198 |
| 2005/0113750 | A1 | 5/2005 | Targell | |
| 2011/0054411 | A1* | 3/2011 | Dowds | A61M 5/3272 604/198 |
| 2013/0204200 | A1 | 8/2013 | Roberts et al. | |
| 2014/0110297 | A1 | 4/2014 | Trotter et al. | |
| 2014/0221934 | A1 | 8/2014 | Janvier et al. | |
| 2014/0303564 | A1* | 10/2014 | Roberts | A61M 5/326 604/198 |
| 2015/0246182 | A1 | 9/2015 | Evans et al. | |
| 2018/0015232 | A1 | 1/2018 | Iwase | |
| 2019/0125978 | A1* | 5/2019 | Daily | A61M 5/3272 |
| 2019/0255258 | A1 | 8/2019 | Dowds et al. | |
| 2019/0351151 | A1* | 11/2019 | Carrel | A61M 5/3272 |
| 2022/0105278 | A1 | 4/2022 | Petit | |

FOREIGN PATENT DOCUMENTS

| | | | |
|---|---|---|---|
| CN | 103108666 | A | 5/2013 |
| EP | 3275489 | A1 | 1/2018 |
| EP | 3278830 | A1 | 2/2018 |
| WO | 2011076280 | A1 | 6/2011 |
| WO | 2011117283 | A2 | 9/2011 |
| WO | 2020173998 | A1 | 9/2020 |

* cited by examiner 180
174
172
170
190
160
140
210
200
220

200
160
140
154
152
120

160
140
152
110
120

SAFETY SYRINGE

CROSS-REFERENCE TO RELATED APPLICATIONS

This application is the United States national phase of International Application No. PCT/US2021/053221 filed Oct. 1, 2021, and claims priority to European Patent Application 20306146.0, entitled "Safety Syringe", filed Oct. 2, 2020, the entire disclosures of which are hereby incorporated by reference in their entirety.

BACKGROUND OF THE INVENTION

Field of the Invention

The present disclosure relates generally to drug delivery devices and, more specifically, to manually-actuated safety syringes.

Description of Related Art

Manually-actuated syringes for drug delivery are typically simple, single-use devices without safety features. The lack of safety features can increase the risk of accidental needle sticks. In addition, many manually-actuated syringes suffer from a risk of premature activation if the syringe is accidentally dropped.

Therefore, a need exists in the art for a manual safety syringe that has increased safety features.

SUMMARY OF THE INVENTION

Provided herein is a safety syringe including a syringe having a barrel having a proximal end, a distal end, and a sidewall therebetween defining an interior, a needle arranged at the distal end of the barrel, and a plunger arranged at the proximal end of the barrel, and a safety subassembly, having a support body having a proximal end, a distal end, and a sidewall therebetween defining an interior, the syringe received within the support body interior, a plurality of finger grips arranged at the proximal end of the support body, and a needle cover arranged at the distal end of the support body and biased distally relative thereto, the needle cover having a proximal end, a distal end configured to contact an injection site of a user, and a sidewall therebetween, the needle cover configured to slide telescopically relative to the support body.

Further embodiments or aspects of the present invention are provided in the following numbered clauses:

Clause 1. A safety syringe having a syringe including a barrel having a proximal end, a distal end, and a sidewall therebetween defining an interior, a needle arranged at the distal end of the barrel, and a plunger arranged at the proximal end of the barrel. The safety syringe also includes a safety subassembly including a support body having a proximal end, a distal end, and a sidewall therebetween defining an interior, the syringe received within the support body interior. The safety subassembly includes a syringe holder received within the support body interior, a plurality of finger grips arranged at the proximal end of the support body, and a needle cover arranged at the distal end of the support body and biased distally relative thereto. The needle cover includes a proximal end, a distal end configured to contact an injection site of a user, and a sidewall therebetween, with the needle cover configured to slide telescopically relative to the support body.

Clause 2. The safety syringe according to clause 1, wherein the needle cover is arranged within the support body.

Clause 3. The safety syringe according to any of clauses 1-2, wherein the needle cover is arranged between the syringe holder and the support body.

Clause 4. The safety syringe according to any of clauses 1-3, wherein, prior to actuation, the needle cover at least partially projects from the distal end of the support body in a first extended position, and wherein the needle is at least partially covered when the needle cover is in the first extended position.

Clause 5. The safety syringe according to any of clauses 1-4, wherein the needle cover is displaced to a first proximal position when the safety syringe is pressed against the injection site.

Clause 6. The safety syringe according to any of clauses 1-5, wherein the needle cover is displaced distally to a second extended position when the safety syringe is lifted from the injection site.

Clause 7. The safety syringe according to any of clauses 1-6, wherein the sidewall of the needle cover comprises a track, and the syringe holder comprises one or more distally-extending arms, the one or more distally-extending arms comprising one or more radially-projecting tabs configured to be received within the track.

Clause 8. The safety syringe according to clause 7, wherein the track and the one or more radially-projecting tabs are configured to prevent the needle cover from being displaced to the first proximal position after the safety syringe is lifted from the injection site.

Clause 9. The safety syringe according to any of clauses 7-8, wherein the track comprises a plurality of branches.

Clause 10. The safety syringe according to clause 9, wherein, as the safety syringe is pressed against the injection site and the needle cover is displaced proximally, the one or more radially-projecting tabs exit a first branch of the track and enter a second branch of the track.

Clause 11. The safety syringe according to clause 10, wherein the track and/or the one or more radially-projecting tabs are configured such that the one or more radially-projecting tabs cannot reenter the first branch when the safety syringe is lifted from the injection site and the needle cover is displaced distally.

Clause 12. The safety syringe according to any of clauses 9-11, wherein the one or more radially-projecting tabs enter a third branch of the track when the safety syringe is lifted from the injection site and the needle cover is displaced distally.

Clause 13. The safety syringe according to any of clauses 9-12, wherein the track comprises a fourth branch laterally offset from the third branch, and the one or more radially-projecting tabs are resiliently biased toward the fourth branch, such that when the needle cover has been displaced distally to the second extended position, the one or more radially-projecting tabs enter the fourth branch of the track.

Clause 14. The safety syringe according to any of clauses 1-13, wherein the needle cover is biased distally by a spring, the needle cover comprises an annular ring extending radially inward at the distal end, and wherein the spring is arranged between the annular ring and the distal end of the syringe barrel.

Clause 15. The safety syringe according to any of clauses 1-14, further including a cap removably attached to the distal end of the support body, wherein the cap is configured to interact with the needle cover such that the needle cover cannot be displaced proximally while the cap is attached to the distal end of the support body.

DESCRIPTION OF THE INVENTION

Figure 1:
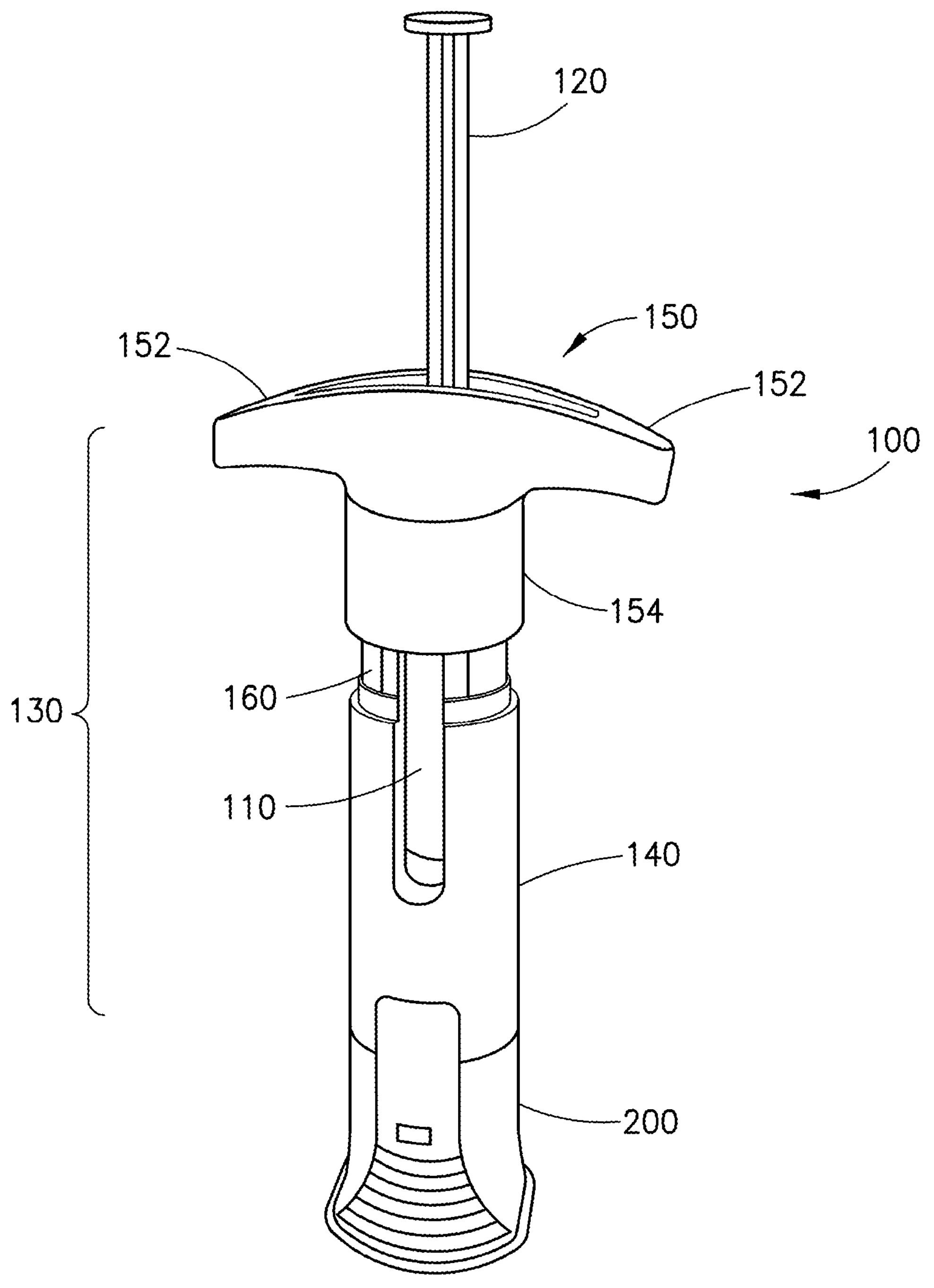
FIG. 1 is a side view of a safety syringe as described herein according to a non-limiting embodiment or aspect.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms “upper”, “lower”, “right”, “left”, “vertical”, “horizontal”, “top”, “bottom”, “lateral”, “longitudinal”, and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Provided herein is a safety syringe having features that reduce the likelihood of a user accidentally coming into contact with the needle, thus decreasing the risk of accidental needle sticks, and having features that reduce the likelihood of the syringe being actuated if the syringe is accidentally dropped prior to use.

With reference to FIG. 1, shown is a non-limiting embodiment or aspect of a safety syringe 100. Safety syringe 100 includes a syringe, for example a pre-filled syringe, having a barrel 110, a plunger 120, and a needle (not shown). Syringe barrel 110 includes a proximal end, a distal end, and a sidewall therebetween defining an interior configured or adapted to contain a medicament. Plunger 120 is arranged at proximal end of barrel 110, and needle (not shown) is arranged at distal end of barrel 110. Barrel 110 can be formed of any suitable material. In non-limiting embodiments or aspects, barrel 110 is formed of glass or a polymer, such as a plastic. Plunger 120 can include an elastomeric stopper (not shown) at a distal end thereof. Stoppers, and elastomeric materials for use in the same, are known to those of skill in the art. In non-limiting embodiments or aspects, a useful stopper is formed of a natural or synthetic rubber. In non-limiting embodiments or aspects, the rubber is butyl rubber (IIR), isoprene rubber (IR), butadiene rubber (BR), styrene-butadiene rubber (SBR), ethylene-propylene rubber (EPM), ethylene-propylene-diene rubber (EPDM), chlorosulphonated polyethylene (CSM), ethylene-vinyl acetate copolymer (EVA), styrene-isoprene rubber (SIR), thermoplastic elastomers, and/or natural rubbers.

In non-limiting embodiments or aspects, the stopper can be formed of an elastomeric copolymer, including, without limitation, thermoplastic elastomers, thermoplastic vulcanizates, styrene copolymers such as styrene-butadiene (SBR or SBS) copolymers, styrene-isoprene (SIS) block polymers, or styrene-isoprene/butadiene (SIBS), in which the content of styrene in the styrene block copolymer ranges from about 10% to about 70%, and preferably from about 20% to about 50%. The elastomeric composition can include, without limitation, antioxidants and/or inorganic reinforcing agents to preserve the stability of the elastomer composition, a vulcanizing agent, a vulcanizing accelerator, a vulcanizing activator, a processing aid, a filler, etc., to maintain and improve the physical properties and heat resistance of the rubber material.

In non-limiting embodiments or aspects, stopper and/or inner facing surface of barrel 110 sidewall can include a coating thereon. Coatings for decreasing friction between a stopper and sidewall and/or for reducing interactions between the elastomeric material of the stopper and the medicament, for example siloxane-based coatings, are known to those of skill in the art, and are described in, for example, U.S. Patent Application Publication Nos. 2014/0221934 and 2014/0110297, the contents of which are incorporated herein by reference in their entirety.

Figure 2:
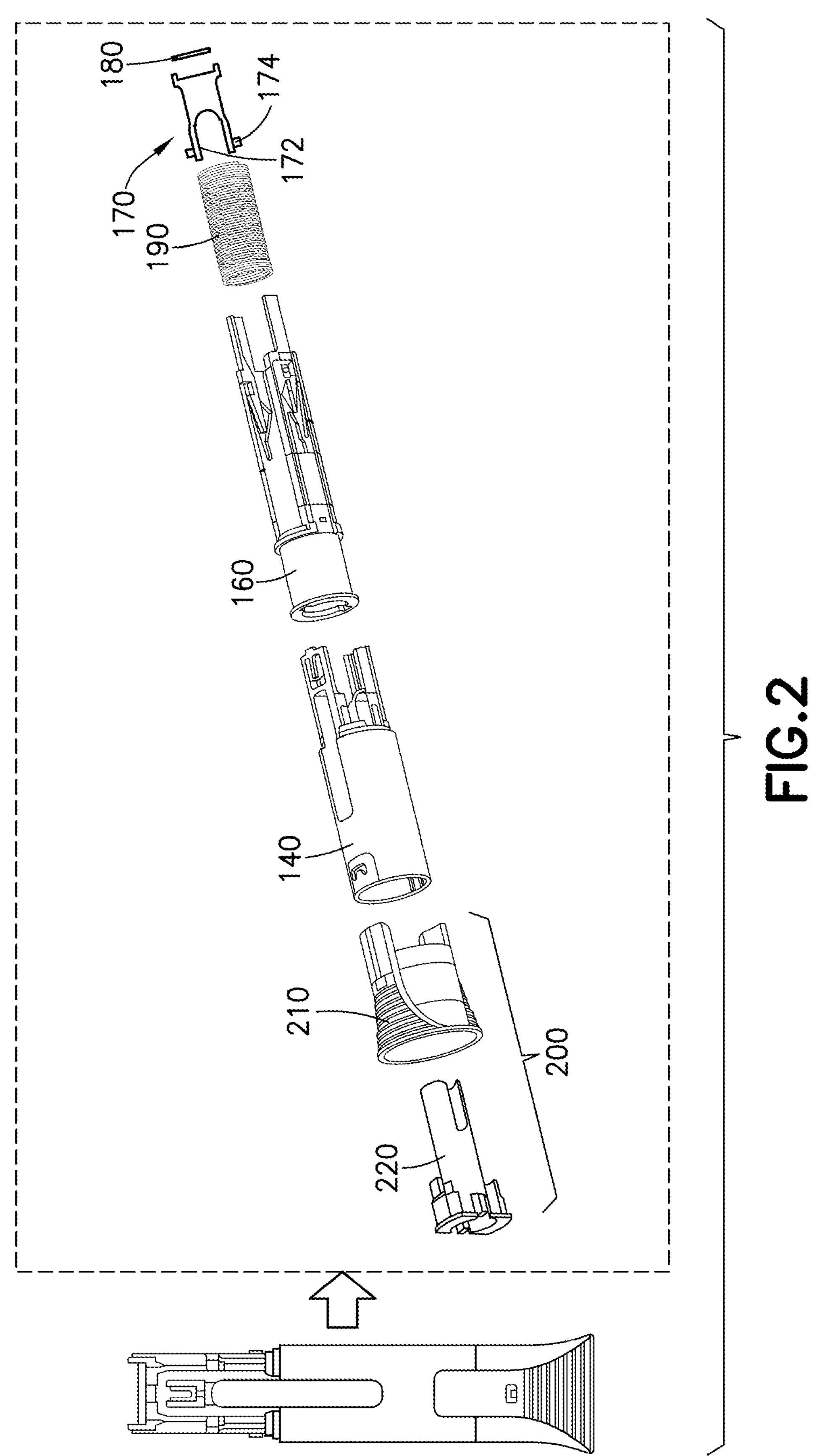
FIG. 2 is a side view and an exploded view of a lower subassembly of a safety syringe as described herein according to a non-limiting embodiment or aspect.

With continuing reference to FIG. 1, and with reference to FIG. 2, a safety syringe 100 as described herein includes a safety subassembly 130. Safety subassembly 130 can include a support body 140 having a proximal end, a distal end, and a sidewall therebetween defining an interior. At least barrel 110 and needle (not shown) of a syringe can be received within the interior of support body 140. Safety subassembly 130 can further include a finger grip assembly 150 including a plurality of finger grips 152 arranged at proximal end of support body 140. Finger grip assembly 150 can be a reversibly attachable component that includes an end 154 configured to be removably attached to proximal end of support body 140. Useful configurations for removable attachment of components are known to those of skill in the art; however, in non-limiting embodiments or aspects, finger grip assembly 150 can be attached to proximal end of support body 140 through a friction fit, a snap fit, a threaded connection, and/or the like.

With continuing reference to FIGS. 1 and 2, safety subassembly 130 includes a needle cover 160 arranged at distal end of support body 140. Needle cover 160 includes a distal end configured to be applied to and to contact an injection site on the skin of a user, a proximal end, and a sidewall therebetween defining an interior in which a needle of a syringe is received. Needle cover 160 can be slidably arranged relative to support body 140, optionally telescopically within the interior of support body 140, or on an outer surface of support body 140. In non-limiting embodiments or aspects, needle cover 160 is biased distally relative to support body 140, for example, by means of return spring

190. In non-limiting embodiments or aspects, needle cover 160 includes an annular ring at distal end thereof. In non-limiting embodiments or aspects, annular ring includes an inner heel, and a distal end of return spring 190 abuts inner heel, and a proximal end of return spring 190 abuts a distal end of syringe barrel 110 and/or a portion of support body 140, thereby applying a distal biasing force to needle cover 160.

With continuing reference to FIG. 2, safety subassembly 130 can further include a syringe holder 170. In non-limiting embodiments or aspects, syringe holder 170 receives a syringe therein, such that a proximal end of syringe barrel 110 (e.g., flanges of a syringe) abuts a proximal end of syringe holder 170 when the safety syringe is assembled. In non-limiting embodiments or aspects, an elastomeric ring 180 is provided between syringe holder 170 and proximal end (e.g., flanges of a syringe) of syringe barrel 110, to reduce the likelihood of breaking and to account for manufacturing tolerances. Elastomeric ring 180 can be a thermoplastic elastomer. Elastomeric ring 180 can be formed of a natural or synthetic rubber. In non-limiting embodiments or aspects, the rubber is butyl rubber (IIR), isoprene rubber (IR), butadiene rubber (BR), styrene-butadiene rubber (SBR), ethylene-propylene rubber (EPM), ethylene-propylene-diene rubber (EPDM), chlorosulphonated polyethylene (CSM), ethylene-vinyl acetate copolymer (EVA), styrene-isoprene rubber (SIR), thermoplastic elastomers, and/or natural rubbers.

In non-limiting embodiments or aspects, stopper can be formed of an elastomeric copolymer, including, without limitation, thermoplastic elastomers, thermoplastic vulcanizates, styrene copolymers such as styrene-butadiene (SBR or SBS) copolymers, styrene-isoprene (SIS) block polymers, or styrene-isoprene/butadiene (SIBS), in which the content of styrene in the styrene block copolymer ranges from about 10% to about 70%, and preferably from about 20% to about 50%. The elastomeric composition can include, without limitation, antioxidants and/or inorganic reinforcing agents to preserve the stability of the elastomer composition, a vulcanizing agent, a vulcanizing accelerator, a vulcanizing activator, a processing aid, a filler, etc., to maintain and improve the physical properties and heat resistance of the rubber material.

In non-limiting embodiments or aspects, syringe holder 170 can include one or more distally-extending arms 172. In non-limiting embodiments or aspects, distally-extending arms 172 are resiliently biased. In non-limiting embodiments or aspects, distally-extending arms 172 can include one or more radially-projecting tabs 174 extending therefrom. In non-limiting embodiments or aspects, one or more radially-projecting tabs 174 project radially inward. In non-limiting embodiments or aspects, one or more radially-projecting tabs 174 project radially outward. The directionality of radially-projecting tabs 174 is dependent on the arrangement of needle cover 160 with respect to syringe holder 170.

Figure 3:
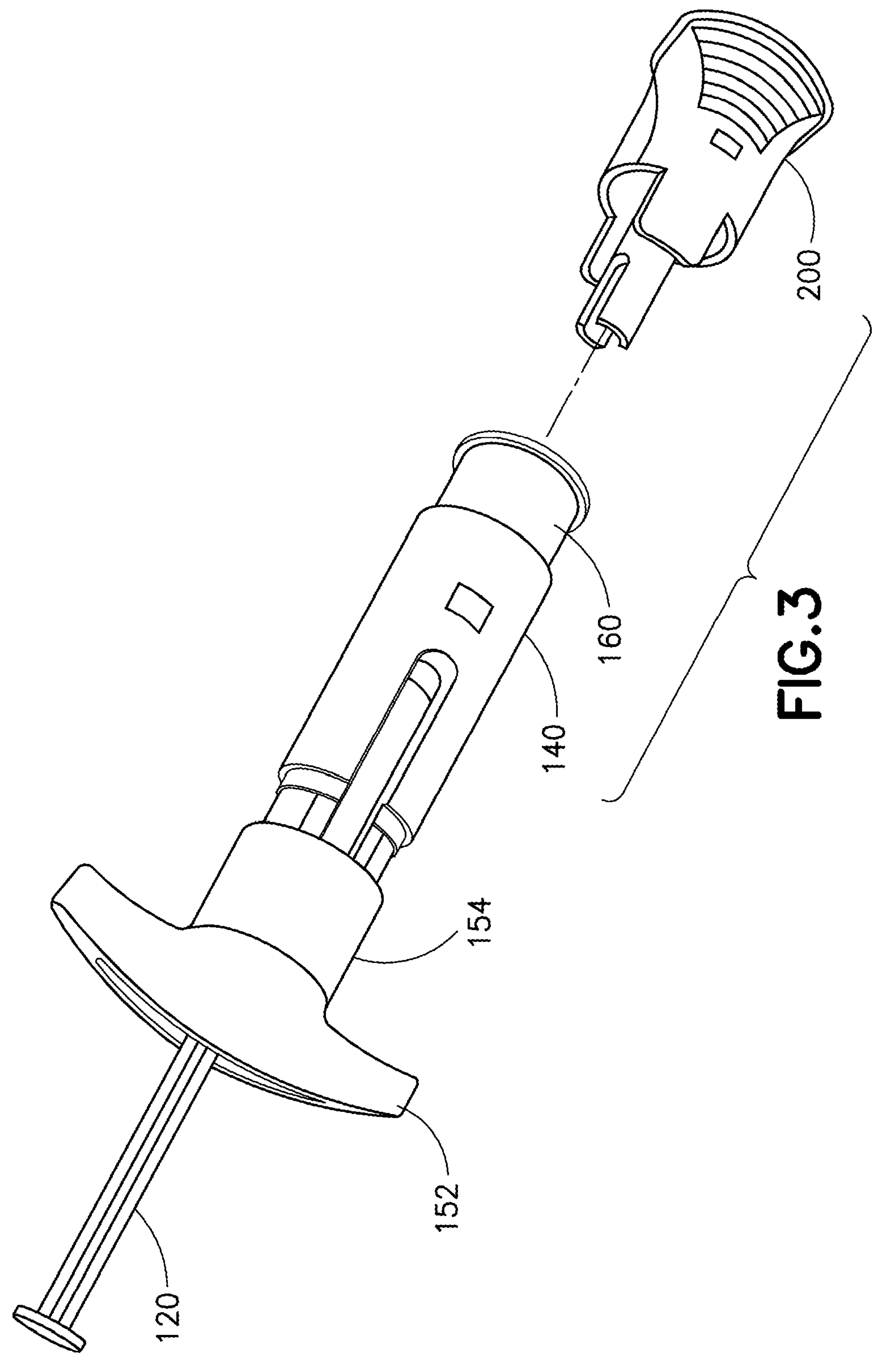
FIG. 3 is a perspective view of a safety syringe as described herein according to a non-limiting embodiment or aspect.

With continuing reference to FIGS. 2 and 3, safety syringe can further include a removable cap assembly 200. Useful configurations for removable attachment of components are known to those of skill in the art; however, in non-limiting embodiments or aspects, cap assembly 200 can be attached to distal end of support body 140 through a friction fit, a snap fit, and/or the like. Cap assembly can include an outer cap 210 and inner retainer 220. Retainer 220 can be used to grip a rigid needle shield (RNS) for removing the same. RNSs are known in the art, and include an inner, elastomeric portion that encases an injection needle, and an outer, rigid plastic portion. Suitable cap assemblies are described in, for example, International Patent Application No. PCT/EP2020/055012, the content of which is incorporated herein by reference in its entirety. In non-limiting embodiments or aspects, retainer 220 grips a RNS (not shown) surrounding needle (not shown) of safety syringe 100. When outer cap 210 is pulled distally away from support body 140, retainer 220 grips the RNS and removes the RNS, rendering the safety syringe 100 ready for use. In non-limiting embodiments or aspects, cap assembly 200, when in place on distal end of support body 140, prevents proximal displacement of needle cover 160.

With regard to assembly of safety syringe 100, a pre-filled syringe is inserted into safety subassembly 130 (minus finger grip assembly 150). Following insertion of the pre-filled syringe, finger grip assembly 150 is attached to proximal end of support body 140, via end 154, for example, by snap fit, friction fit, threaded connection, or the like, thus providing safety syringe 100.

Figure 4:
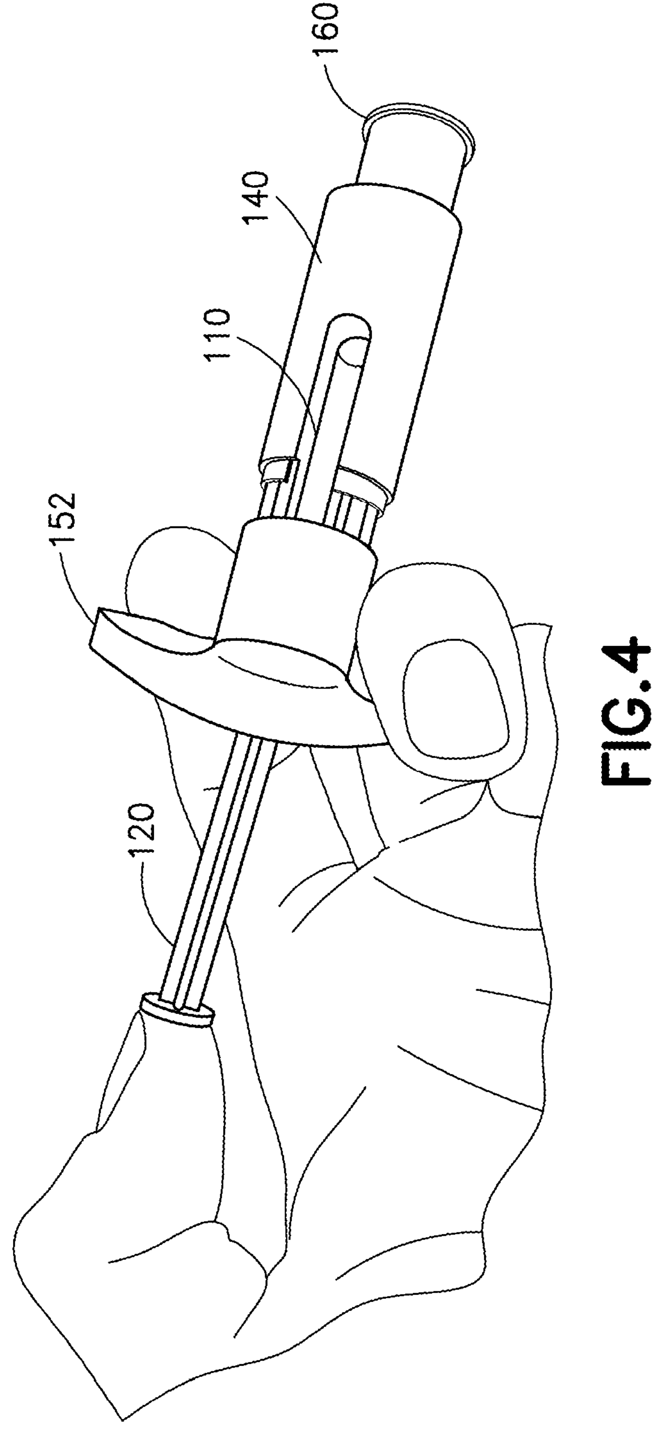
FIG. 4 is a perspective view of a safety syringe as described herein according to a non-limiting embodiment or aspect.
Figure 5:
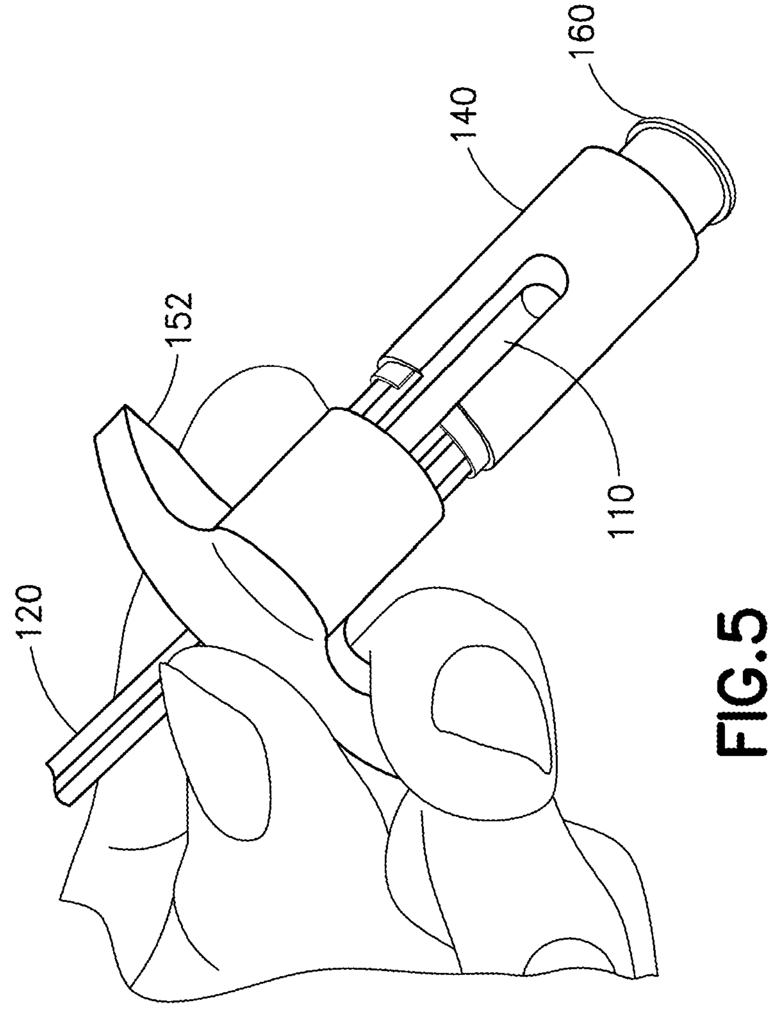
FIG. 5 is a perspective view of a safety syringe as described herein according to a non-limiting embodiment or aspect.

With reference to FIGS. 4 and 5, shown is a non-limiting embodiment or aspect of actuation of safety syringe 100. Cap assembly 200 (and, optionally, any RNS) has been removed, and safety syringe 100 is ready for use. Distal end of needle cover 160 is applied to a site of injection on a user. Application of pressure causes needle cover 160 to be displaced proximally, exposing needle (not shown). A user, with fingers on finger grips 152 and thumb on a proximal-most end of plunger 120, can then actuate plunger 120 to deliver medicament to the injection site.

Figure 6A:
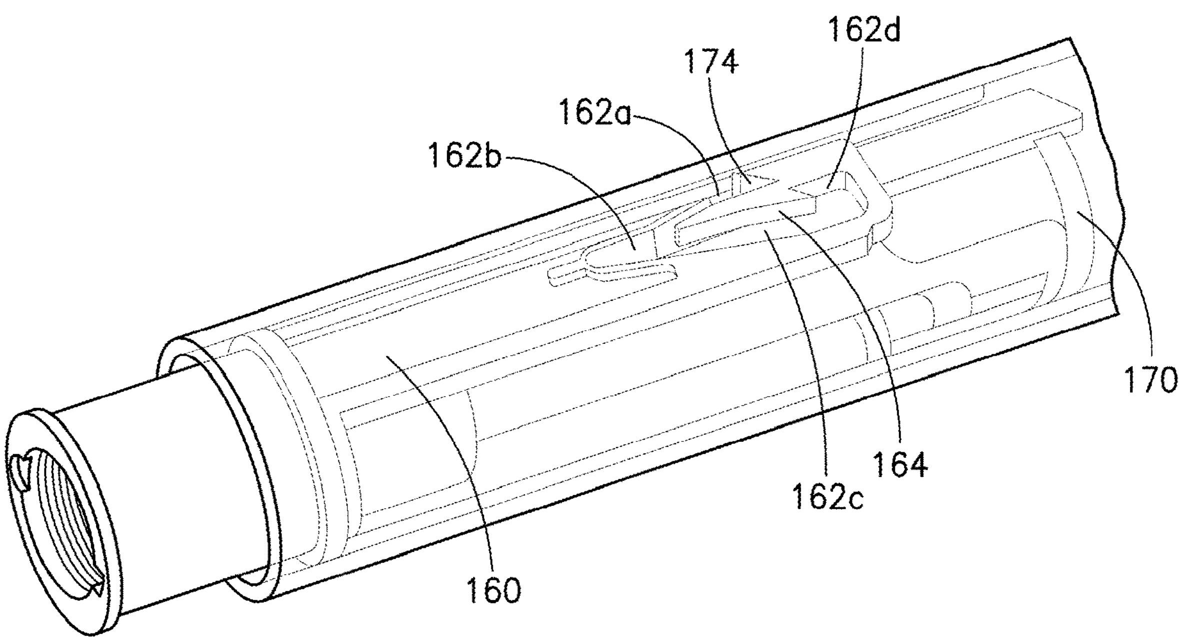
FIGS. 6A-6C am a perspective view of a safety syringe as described herein according to a non-limiting embodiment or aspect.
Figure 6B:
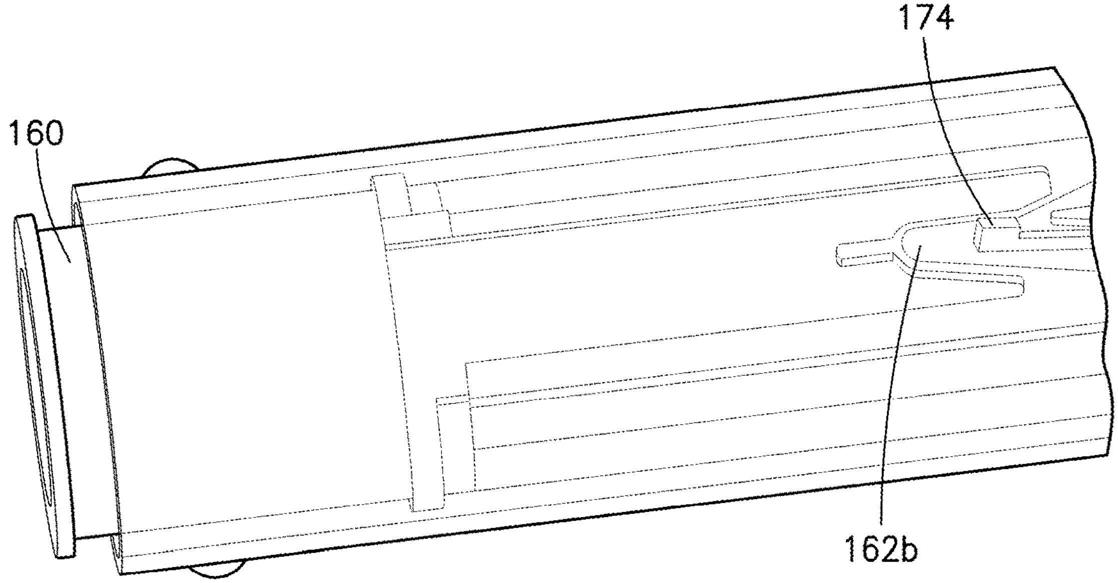
Figure 6C:
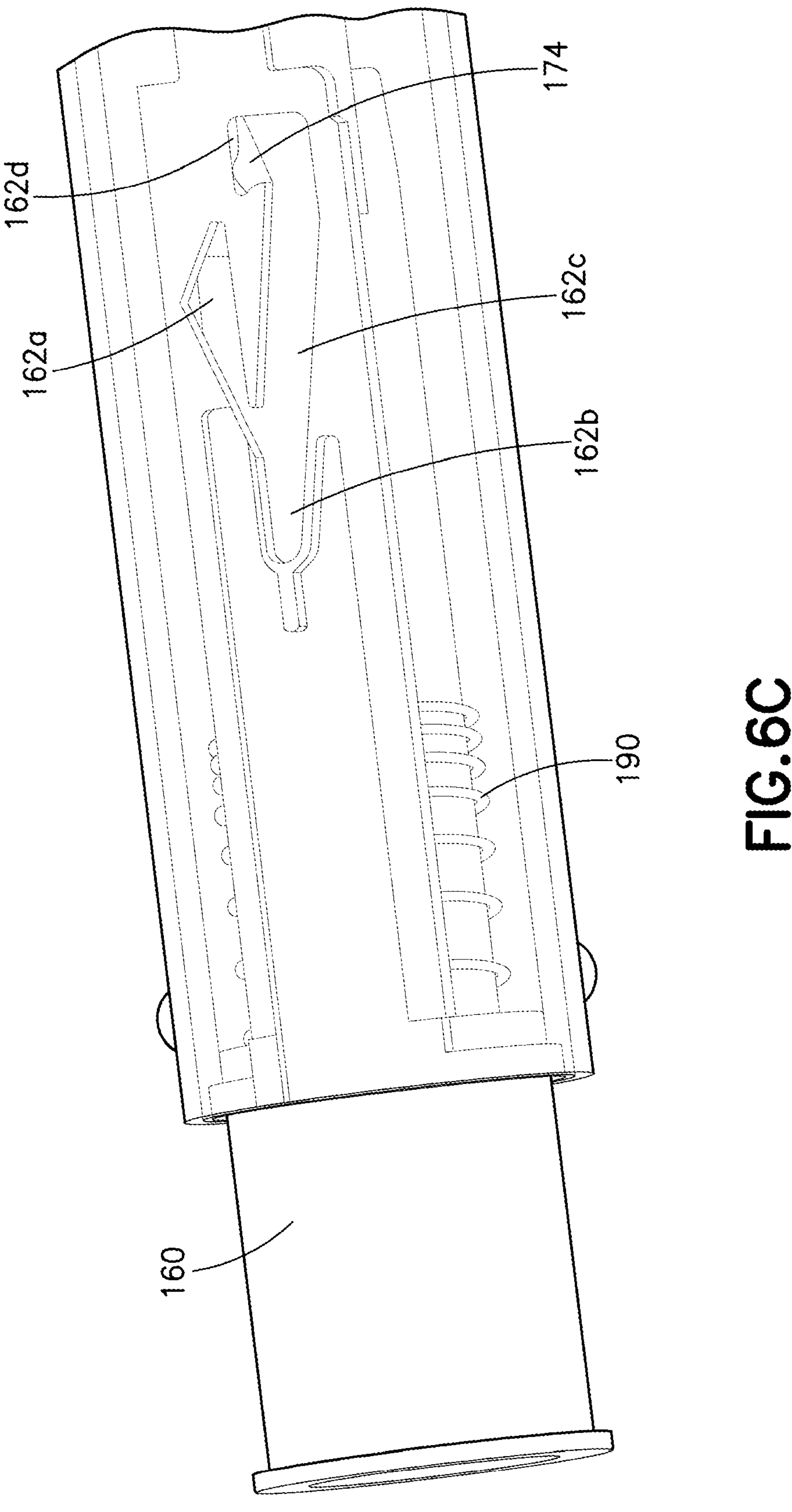

With reference to FIGS. 6A-6C, shown is a non-limiting embodiment or aspect of needle cover 160, in which needle cover 160 can be locked such that a needle (not shown) cannot be exposed following proximal displacement of needle cover 160. In FIG. 6A, needle cover 160 is shown in a first extended positon, in which needle (not shown) of safety syringe 100 is enclosed by needle cover 160. In the non-limiting embodiment or aspect that is illustrated, syringe holder 170 includes one or more distally-extending arms 172, and one or more radially-projecting tabs 174 extending therefrom. In the non-limiting embodiment or aspect that is illustrated, needle cover 160 includes a track 162 in sidewall 164 thereof. While only a single track 162 is shown, it is to be appreciated that needle cover 160 may include two opposed tracks, each receiving one or more radially-projecting tabs 174.

One or more radially-projecting tabs 174 and track 162 are configured to interact, such that one or more radially-projecting tabs 174 ride within track 162 as needle cover 160 is displaced proximally, for example when applied to an injection site, and displaced distally, for example, when lifted from an injection site. In non-limiting embodiments or aspects, track 162 includes a plurality of branches (162*a*-162*d*), for example as shown in FIGS. 6A-6C. In non-limiting embodiment or aspects, one or more of a plurality of branches of track 162 may be angled relative to one or more of the other branches. In non-limiting embodiments or aspects, in a pre-actuation position, when needle cover 160 is in a first extended position, one or more radially-projecting tabs 174 are positioned within a first branch 162*a* of track 162. In non-limiting embodiments or aspects, first branch 162*a* of track 162 is separated from other branches by a sidewall 164.

With reference to FIG. 6B, shown is a non-limiting embodiment or aspect of needle cover 160 and one or more radially-projecting tabs 174, when needle cover 160 is displaced proximally, for example, in preparation for drug delivery to a site of injection. Needle cover 160 has been displaced to such a degree that one or more radially-projecting tabs 174 abut or nearly abut a distal-most end of track 162, in a second branch 162*b* thereof.

With reference to FIG. 6C, shown is a non-limiting embodiment or aspect of needle cover 160 and one or more radially-projecting tabs 174 when needle cover 160 is displaced distally by return spring 190 to a second extended position, in which needle is enclosed by needle cover 160. One or more radially-projecting tabs 174 cannot reenter the first branch 162*a* of track 162 as needle cover 160 is displaced distally by return spring 190, because of the arrangement of one or more radially-projecting tabs 174 and/or sidewall 164. In non-limiting embodiments or aspects, a proximal-facing surface of one or more radially-projecting tabs 174 is angled, such that resilient, distally-extending arm 172 on which one or more radially-projecting tabs 174 are arranged, is displaced laterally and proceeds along sidewall 164 into a third branch 162*c* of track 162. In non-limiting embodiments or aspects, for example, as shown in FIGS. 6A-6C, sidewall 164 is angled such that distally-extending arm 172 is displaced laterally as needle cover 160 is displaced distally. As shown in FIG. 6C, when needle cover 160 has been displaced distally to a second extended position, the resiliently-biased nature of distally-extending arm 172, and the laterally offset (from third branch 162*c*) configuration of fourth branch 162*d* of track 162, allows the resiliently-biased, distally-extending arm 172 to return to a relaxed position, in which one or more radially-projecting tabs 174 is positioned behind sidewall 164. In this configuration, while needle cover 160 can be displaced proximally, the interaction between one or more radially-projecting tabs 174 and sidewall 164 prevents proximal displacement of needle cover 160 to such a degree that needle (not shown) is exposed.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A safety syringe comprising:

a syringe comprising:

a barrel having a proximal end, a distal end, and a sidewall therebetween defining an interior;

a needle arranged at the distal end of the barrel; and a plunger arranged at the proximal end of the barrel; and a safety subassembly, comprising:

a support body having a proximal end, a distal end, and a sidewall therebetween defining an interior, the syringe received within the support body interior;

a syringe holder received within the support body interior and comprising one or more distally-extending arms, the one or more distally-extending arms comprising one or more radially-projecting tabs;

a plurality of finger grips arranged at the proximal end of the support body; and a needle cover arranged within the support body at the distal end of the support body and biased distally relative thereto, the needle cover comprising a proximal end, a distal end configured to contact an injection site of a user, and a sidewall therebetween comprising a track therein, the track configured to receive the one or more radially-projecting tabs and comprising a plurality of branches, the needle cover configured to slide telescopically relative to the support body wherein prior to actuation, the needle cover at least partially projects from the distal end of the support body in a first extended position, and wherein the needle is at least partially covered when the needle cover is in the first extended position, characterized in that, as the safety syringe is pressed against the injection site and the needle cover is displaced proximally, the one or more radially-projecting tabs exit a first branch of the track and enter a second branch of the track;

as the safety syringe is lifted from the injection site, the one or more distally-extending arms are displaced laterally, in a direction perpendicular to the radially-projecting tabs, from a relaxed position such that the one or more radially-projecting tabs enter a third branch of the track and the needle cover is displaced distally; and the one or more radially-projecting tabs are resiliently biased toward a fourth branch that is laterally offset from the third branch, such that when the needle cover has been displaced distally to a second extended position, the one or more radially-projecting tabs enter the fourth branch of the track where the one or more distally-extending arms are laterally returned to the relaxed position.

2. The safety syringe according to claim 1, wherein the needle cover is arranged between the syringe holder and the support body.

3. The safety syringe according to claim 1, wherein the needle cover is displaced to a first proximal position when the safety syringe is pressed against the injection site.

4. The safety syringe according to claim 1, wherein the track and the one or more radially-projecting tabs are configured to prevent the needle cover from being displaced to the first proximal position after the safety syringe is lifted from the injection site.

5. The safety syringe according to claim 1, wherein the track and/or the one or more radially-projecting tabs are configured such that the one or more radially-projecting tabs cannot reenter the first branch when the safety syringe is lifted from the injection site and the needle cover is displaced distally.

6. The safety syringe according to claim 1, wherein:

the needle cover is biased distally by a spring;

the needle cover comprises an annular ring extending radially inward at the distal end; and wherein the spring is arranged between the annular ring and the distal end of the syringe barrel.

* * * * *